(12) United States Patent
Hines et al.

(10) Patent No.: US 6,582,365 B1
(45) Date of Patent: Jun. 24, 2003

(54) ADVANCED SENSOR SYSTEMS FOR BIOTELEMETRY

(75) Inventors: John W. Hines, Sunnyvale, CA (US); Christopher J. Somps, East Lyme, CT (US); Robert D. Ricks, Newark, CA (US); Carsten W. Mundt, San Martin, CA (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 0 days.

(21) Appl. No.: 09/350,736

(22) Filed: Jul. 9, 1999

Related U.S. Application Data (60) Provisional application No. 60/094,152, filed on Jul. 9, 1998, provisional application No. 60/104,774, filed on Oct. 19, 1998, and provisional application No. 60/104,775, filed on Oct. 19, 1998.

(51) Int. Cl.$^7$ ................................................ A61B 5/00
(52) U.S. Cl. ........................ 600/300; 128/903; 600/508; 600/304
(58) Field of Search ................................ 600/300–301, 600/508, 549, 547, 304, 551; 128/903, 920; 607/32, 60, 22; 340/870.11–870.14, 500, 505; 455/100

(56) References Cited

U.S. PATENT DOCUMENTS

| | | |
|---|---|---|
| 3,949,388 A | 4/1976 | Fuller |
| 4,127,110 A | 11/1978 | Bullara |
| 4,431,004 A | 2/1984 | Bessman et al. |
| 4,519,401 A | 5/1985 | Ko et al. |
| 4,543,955 A | 10/1985 | Schroeppel |

(List continued on next page.)

OTHER PUBLICATIONS

C. Mundt, R. Ricks, C. J. Somps, J. W. Hines, "Advanced Sensor Systems for Improved Labor and Fetal Monitoring", ISA EXPO/98 Conference, International Society for Measurement and Control, Houston, TX, Oct. 19–22, 1998 vol. 2, Part 2, pp. 83–93.

*Primary Examiner*—Max F. Hindenburg
*Assistant Examiner*—Michael Astorino
(74) *Attorney, Agent, or Firm*—Robert M. Padilla; Kenneth L. Warsh; Carla M. Wong (57) ABSTRACT

The present invention relates to telemetry-based sensing systems that continuously measures physical, chemical and biological parameters. More specifically, these sensing systems comprise a small, modular, low-power implantable biotelemetry system capable of continuously sensing physiological characteristics using implantable transmitters, a receiver, and a data acquisition system to analyze and record the transmitted signal over several months. The preferred embodiment is a preterm labor and fetal monitoring system.

Key features of the invention include Pulse Interval Modulation (PIM) that is used to send temperature and pressure information out of the biological environment. The RF carrier frequency is 174–216 MHz and a pair of RF bursts (pulses) is transmitted at a frequency of about 1–2 Hz. The transmission range is 3 to 10 feet, depending on the position of the transmitter in the body and its biological environment. The entire transmitter is encapsulated in biocompatible silicone rubber. Power is supplied by on-board silver-oxide batteries. The average power consumption of the current design is less than 30 $\mu$W., which yields a lifetime of approximately 6–9 months. Chip-on-Board technology (COB) drastically reduces the size of the printed circuit board from 38×28 mm to 22×8 mm. Unpackaged dies are flip-chip bonded directly onto the printed circuit board, along with surface mount resistors and capacitors. The invention can monitor additional physiological parameters including, but not limited to, ECG, blood gases, glucose, and ions such as calcium, potassium, and sodium.

14 Claims, 10 Drawing Sheets

U.S. PATENT DOCUMENTS

| | | | |
|---|---|---|---|
| 4,556,063 A | * 12/1985 | Thompson et al. | ......... 129/903 |
| 4,703,756 A | 11/1987 | Gough et al. | |
| 4,796,641 A | 1/1989 | Mills et al. | |
| 4,844,076 A | 7/1989 | Lesho et al. | |
| 4,903,701 A | * 2/1990 | Moore et al. | ................. 607/60 |
| 5,188,109 A | 2/1993 | Saito | |
| 5,312,446 A | * 5/1994 | Holschbach et al. | ............ 607/9 |
| 5,372,133 A | 12/1994 | Esch et al. | |
| 5,373,852 A | 12/1994 | Harrison et al. | |
| 5,538,005 A | 7/1996 | Harrison et al. | ............ 128/698 |
| 5,755,671 A | * 5/1998 | Albrecht et al. | ............ 600/516 |
| 6,229,454 B1 | * 5/2001 | Heikkila et al. | ............ 600/508 |

* cited by examiner

(See Fig. 7B)

FIG. 8

ADVANCED SENSOR SYSTEMS FOR BIOTELEMETRY

CROSS-REFERENCE TO RELATED APPLICATIONS

This application claims the benefit of U.S. Provisional Application Nos. 60/094,152, filed Jul. 9, 1998, entitled "Implantable Biotelemetry System for Preterm Labor and Fetal Monitoring", 60/104,774, filed Oct. 19, 1998, entitled "Implantable Pill-Transmitters for Physiological Monitoring", and 60/104,775, filed Oct. 19, 1998, entitled "Data Acquisition and Analysis Program for Physiological Monitoring" all of which are herein incorporated by reference.

ORIGIN OF INVENTION

The invention described herein was made by employees of the United States Government and under the following NASA contract, NAS2-13767; thus, it may be manufactured and used by or for the Government for governmental purposes without payment of any royalties thereon or therefore.

BACKGROUND OF INVENTION

A. Technical Field of the Invention

The present invention relates to telemetry-based sensing systems that measure physical, chemical and biological parameters. More specifically, these sensing systems comprise a small, modular, low-power implantable biotelemetry system capable of continuously sensing physiological characteristics using implantable transmitters, a receiver, and a data acquisition system to analyze and record the transmitted signal over several months. The preferred embodiment is a preterm labor and fetal monitoring system.

B. Description of the Prior Art

A number of fetuses suffer from diaphragmatic hernia, a condition in which a hole in the diaphragm allows internal organs to shift from the abdominal cavity into the chest cavity. The lungs have insufficient space to develop and about 60 percent of children born with this condition die. An open hysterotomy (similar to a Cesarean section) surgery to access the fetus is used to correct this anomaly. Recently, pediatric surgeons at the UC San Francisco Fetal Treatment Center (FTC) have developed a new surgical procedure to treat diaphragmatic hernia in fetuses through a minimally invasive procedure using endoscopic techniques. With this approach, in utero surgical procedures are conducted through a number of small openings in the uterus, the largest being about 10 mm. This approach has been developed to minimize postoperative preterm labor, a problem encountered in all patients who undergo fetal surgery. Accurate monitoring of uterine contractions in the postoperative period is critical to develop medications that can inhibit the progression of preterm labor.

Among other applications, the inventive concepts disclosed herein can be applied to the general problem of preterm births, which currently account for over seven percent of all live births and with associated costs running into the billions of dollars each year. Various attempts have been made to monitor fetal characteristics by telemetry. U.S. Pat. Nos. 5,431,171 and 5,538,005 issued to Harrison et al. disclose a remote sensing unit with a transceiver that outputs the sampled fetal temperature and electrocardiogram signals to an antenna external to the patient's body. However, the packaging technique of the prior art biotelemetry units resulted in a unit too large to be safely and conveniently implanted into a patient and with too short an operating time for what is necessary to monitor recovery. Further, these prior art units are of modular in that they operate on only one frequency and they do not measure electrochemical or biological parameters.

In the field of laparoscopic surgery generally, there is a need for implantable biotelemetry devices that continuously measure physical, chemical and biological parameters in vivo for an extended period of monitoring. A pill-sized biotelemetry transmitter small enough to be introduced into the patient through a 10 mm trocar is needed. More specifically, such a device could provide pediatric surgeons with otherwise unattainable information on intra-uterine pressure and temperature as well as fetal heart rate and tissue pH, parameters critical to the successful monitoring and evaluation of postoperative preterm labor and fetal health and well-being.

SUMMARY OF THE INVENTION

The present invention provides a transmitter for measuring at least one physiological characteristic from a position inside a subject and transmitting physiological data to a remote location. The transmitter includes a first sensor for a first physiological characteristic and a second sensor for a second physiological characteristic. The first sensor drives a gated integrator that integrates to a fixed threshold voltage. The magnitude of the first physiological characteristic determines the integration time of the gated integrator. A comparator detects when the threshold voltage is exceeded and converts the first physiological characteristic into a pulse of varying width (nominal width 5–15 ms). An edge detector converts each edge of the pulse into a short pulse (nominal width hundreds of microseconds). The short pulses are used to enable an RF oscillator to transmit the physiological data to the remote location. This process is repeated every 100 to 500 ms depending on the value sensed by the second physiological sensor. The one-shot is triggered on the falling edge of the comparator output. The first physiological characteristic is encoded by the time between the two short pulses and the second physiological characteristic is encoded by the repetition rate of the short pulse pairs.

The telemetry system of the present invention for measuring at least one physiological characteristic transmits the individual characteristics to a remote location. The system includes a transmitter for transmitting physiological data as a pulse interval modulated signal. A receiver is configured for receiving and converting the pulse interval modulated signal into a digital pulse stream. The receiver decodes the digital pulse stream into voltages proportional to the individual characteristics of the physiological data. A data acquisition card is configured to digitize the physiological data. A signal processing system is included for the display and storage of the individual characteristics of the physiological data over time.

Advantages of the present invention include a biotelemetric system that utilizes a small, modular, low-power/long-life, pill-shaped implantable biotelemeter capable of continuously sensing physiological characteristics over a period of up to nine months or slightly more. Further, the present invention discloses the integration of ion-selective microelectrode sensors into a biotelemetric system.

The present invention also discloses a method of measuring at least one physiological characteristic from a position inside a subject and transmitting the individual characteristics as physiological data to a remote location. The method includes the steps of: sensing and transmitting physiological data in a pulse modulated signal to the remote location; receiving and converting the pulse interval modulated signal into a digital pulse stream into voltages proportional to the individual characteristics of the physiological data; digitizing the physiological data; and displaying and storing of the individual characteristics of the physiological data over time.

BRIEF DESCRIPTION OF THE DRAWINGS

The drawings that form a part of the disclosure herein.

DETAILED DESCRIPTION OF THE DRAWINGS

The present invention provides a biotelemetry system for measuring physiological or physical characteristics in real time over an extended period of at least several months. A pill transmitter for measuring pressure and temperature has been built and tested. A functional prototype of the pH and temperature pill transmitter has also been built and tested. All of the pill transmitters, including for pH, provide continuous monitoring of the physiological characteristic of interest. Additional circuit designs for sensing heart rate, ECG, EMG, glucose and dissolved oxygen have been simulated. Ion-selective microelectrodes are used for sensing pH and ions.

Figure 1:
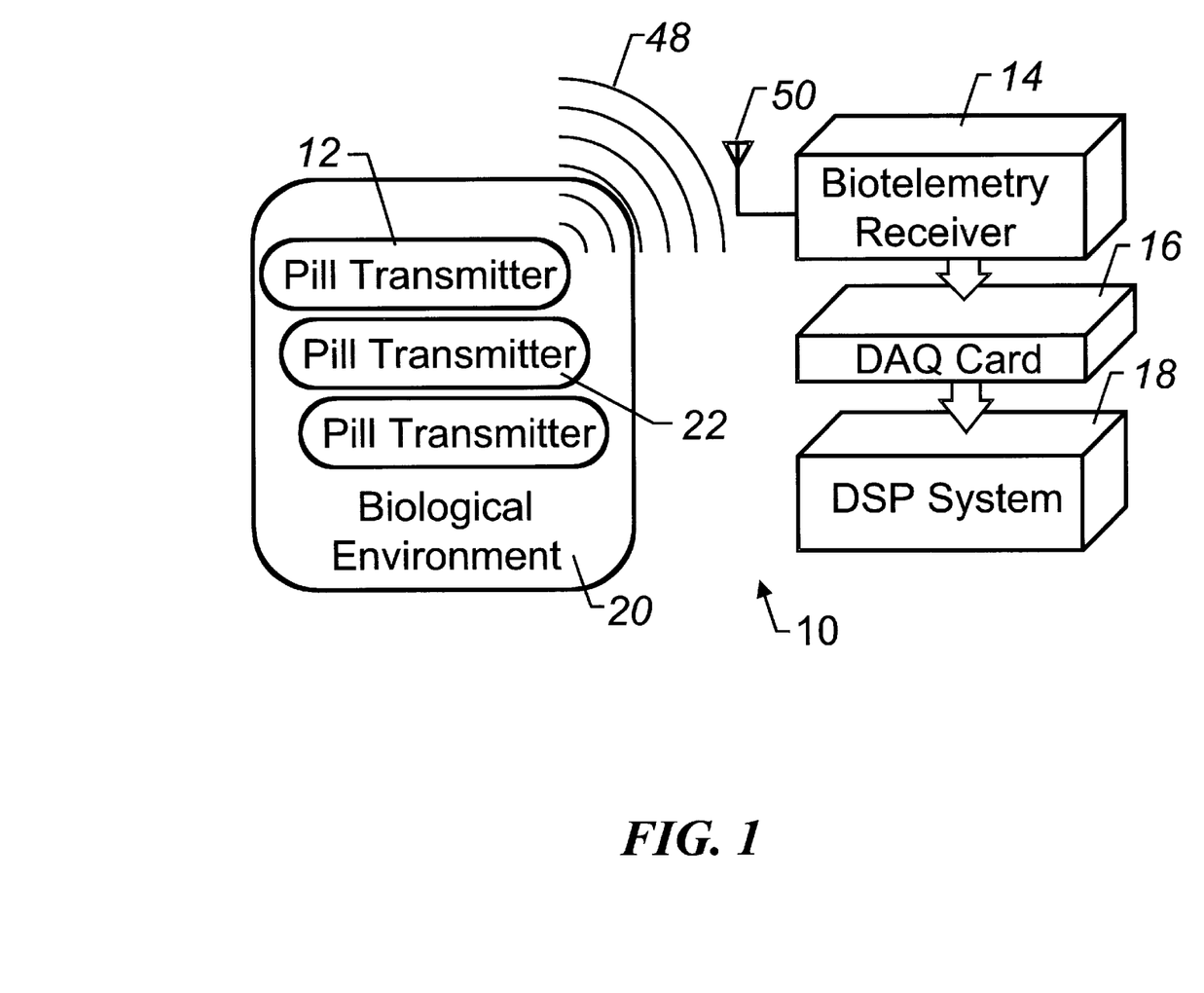
FIG. 1 shows a functional block diagram of a biotelemetry system in accordance with the present invention.

As illustrated in FIG. 1, a preferred embodiment of the present invention provides a biotelemetry system 10 that consists of at least four main components: one or more transmitters like 12, a biotelemetry receiver 14, a data acquisition circuit 16, and a digital signal processing system 18.

One or more additional transmitters like 22 can be used to simultaneously measure a plurality of physiological or physical characteristics or the same characteristic from several locations. Such additional transmitters transmit at different frequencies so that the physiological characteristic data from multiple transmitters can be transmitted simultaneously. Several such characteristics (one to eight) can also be combined into one transmitter. As used herein the term physiological includes physical characteristics as well.

The transmitter 12 is surgically implanted, ingested, or otherwise inserted into a biological environment 20 such as a human, animal or the like. Preferably, minimally invasive surgical techniques, such as endoscopy, implant the transmitter 12 through openings of about 10 mm in diameter to monitor and evaluate postoperative preterm labor and fetal health. To fulfill this need, the transmitter 12 must have small physical dimensions that measure 9 mm or less in diameter with an overall length of preferably less than 35 mm. As specifically illustrated in FIG. 2, at least one printed circuit board (PCB) 24 supports a first sensor 28 such as a piezoresistive pressure transducer for sensing changes in pressure within the interior cavity 29 defined by a housing 31. Preferably, the PCB 24 supports a second sensor 26, such as a thermistor, for measuring absolute temperature. The PCB 24 uses Chip-on-Board technology (COB) and surface mount technology. The pressure transducer is wire bonded and all other dies flip-chip bonded directly to the PCB. The overall dimensions of the PCB 24 are about 8 mm in width and about 22 mm in length.

Figure 2:
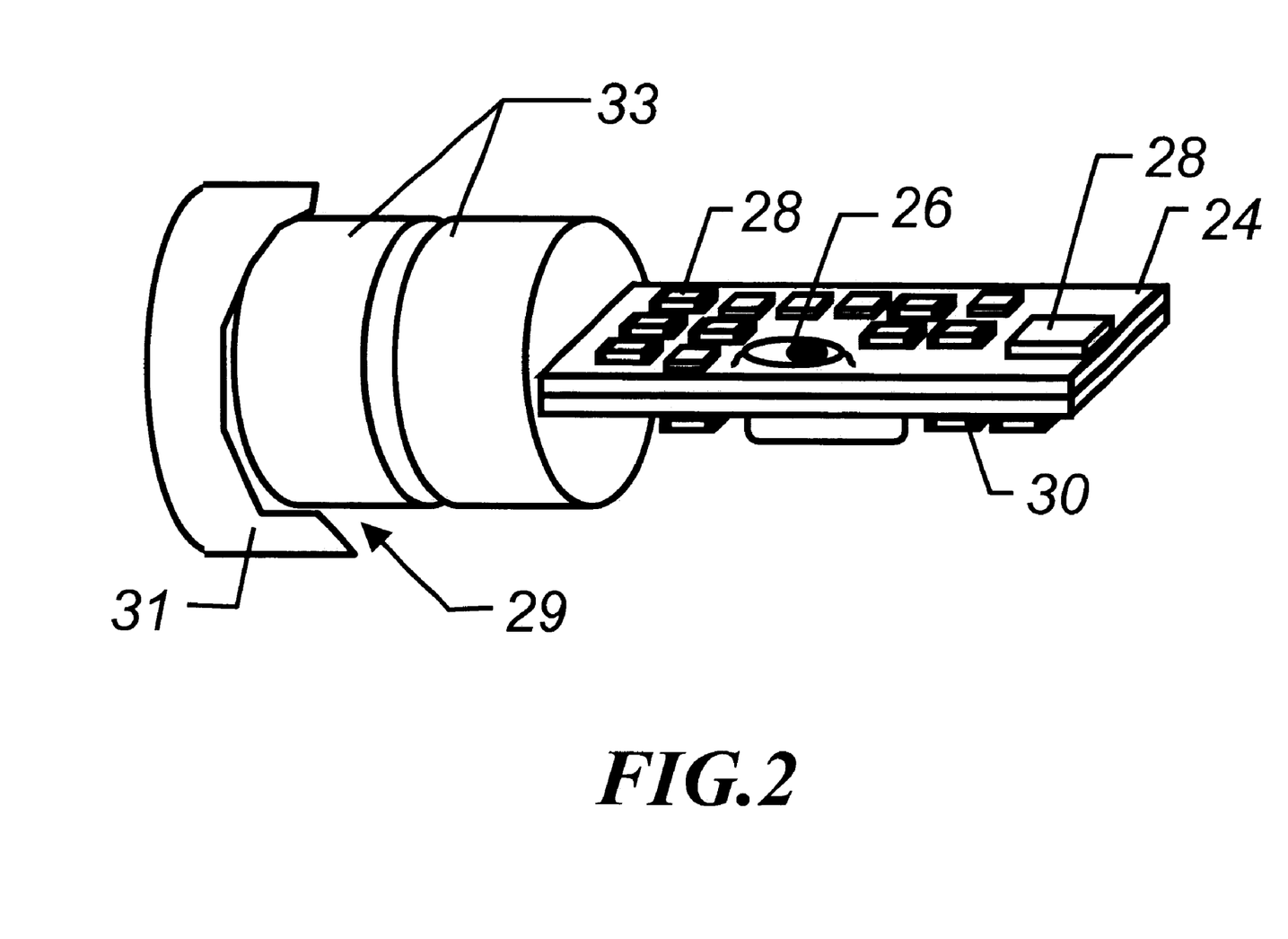
FIG. 2 shows a side view of a transmitter of the present invention before encapsulation in a biocompatible material.

Preferably, the PCB 24 supporting the sensors 26 and 28 is mounted to the back side of an RF oscillator PCB 30. The RF oscillator PCB 30 could be integrated with the sensors 26 and 28 onto one PCB. However, it is preferred to provide a separate RF oscillator PCB to enable the same RF oscillator PCB to be used with different sensors supported on the sensor PCB 24. Further, locating the RF oscillator circuit on a separate board isolates the oscillator circuit from the remaining components thereby reducing noise.

Power is supplied on-board to the transmitter 12 in FIG. 2 by one or more commercially available silver oxide batteries 33 at one end of the PCBs 24 and 30. The average power consumption of the design of the preferred embodiments is less than about 30 $\mu$W, which yields an operating lifetime of approximately 6–9 months using two 70 mAh silver oxide batteries. All parts of the transmitter 12 are encapsulated in a silicone rubber or other biocompatible material. While the pressure and temperature sensors are encapsulated, it should be pointed out that pH and other ion-selective microelectrode sensors have a PVC catheter that protrudes out of the encapsulation to contact the characteristic of interest. Likewise, the heart rate sensor has two electrode leads to obtain the ECG signal.

Figure 3:
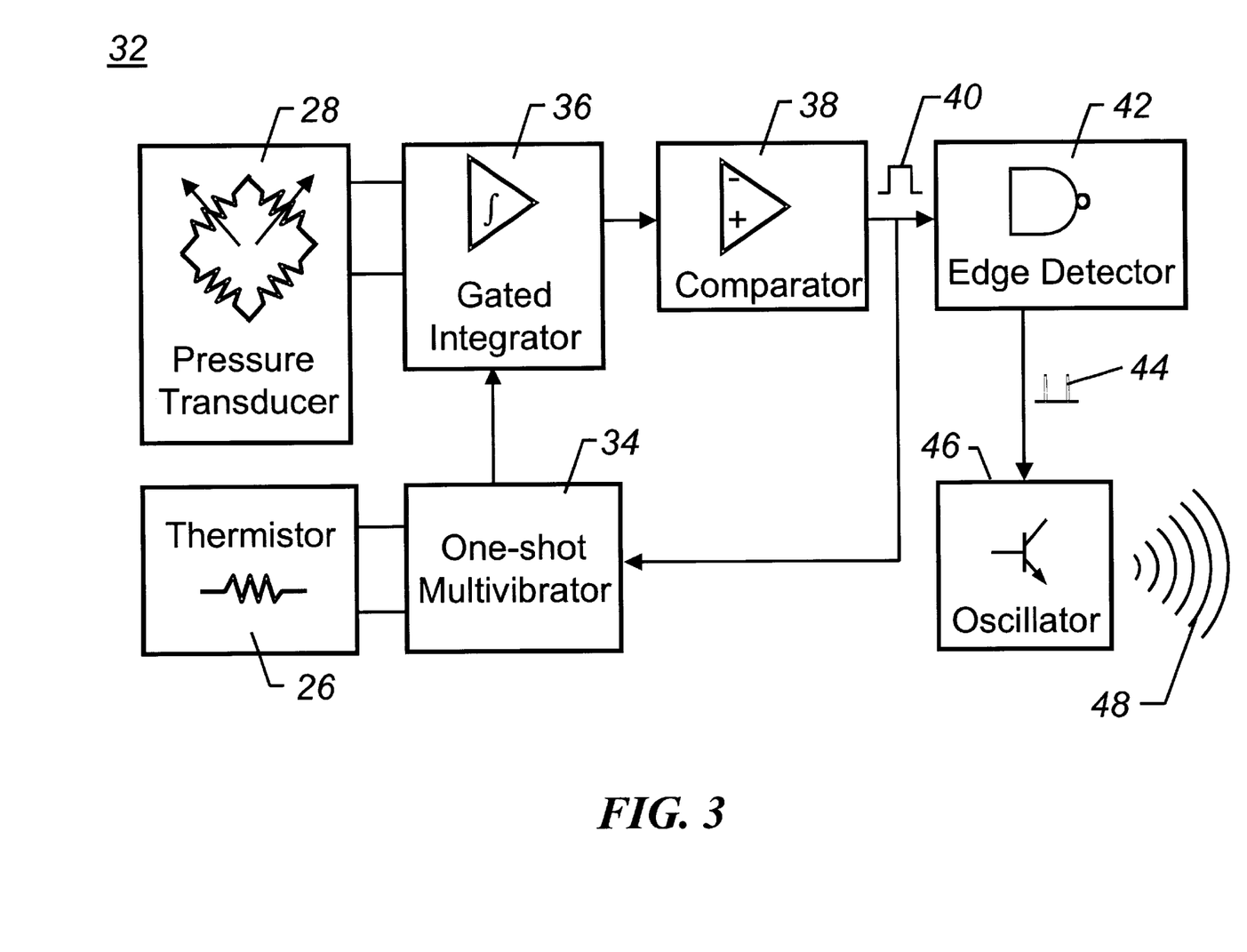
FIG. 3 shows a block diagram of a pressure/temperature transmitter circuit of a preferred embodiment.

The transmitter circuit 32 is illustrated in FIG. 3 where two sensors are used—a first sensor 28 for a first physiological characteristic and a second sensor 26 for a second physiological characteristic. While FIG. 3 shows a the first sensor 28 to be a pressure transducer and the second sensor 26 to be a thermistor, other sensors could replace these sensors to measure other physiological characteristics. The first sensor 28 drives a gated integrator 36 that integrates to a fixed threshold voltage. The magnitude of the first physiological characteristic determines the integration time of the gated integrator 36. A comparator 38 detects when the threshold voltage is exceeded and converts the first physiological characteristic into a pulse 40 of varying width (nominal width 5–15 ms). An edge detector 42 converts each edge of the pulse into a short pulse 44 (nominal width in 1s the hundreds of microseconds). The short pulses 44 are used to enable an RF oscillator 46 to transmit electrical signals 48 corresponding to the physiological data to the remote location. This process is repeated every 100 to 500 ms depending on the value sensed by the second physiological sensor which controls the time constant of the one-shot multivibrator 34. The one-shot multivibrator 34 is triggered on the falling edge of the comparator 38 output. The first physiological characteristic is encoded by the time between the two short pulses and the second physiological characteristic is encoded by the repetition rate of the pulse pairs.

Figure 4:
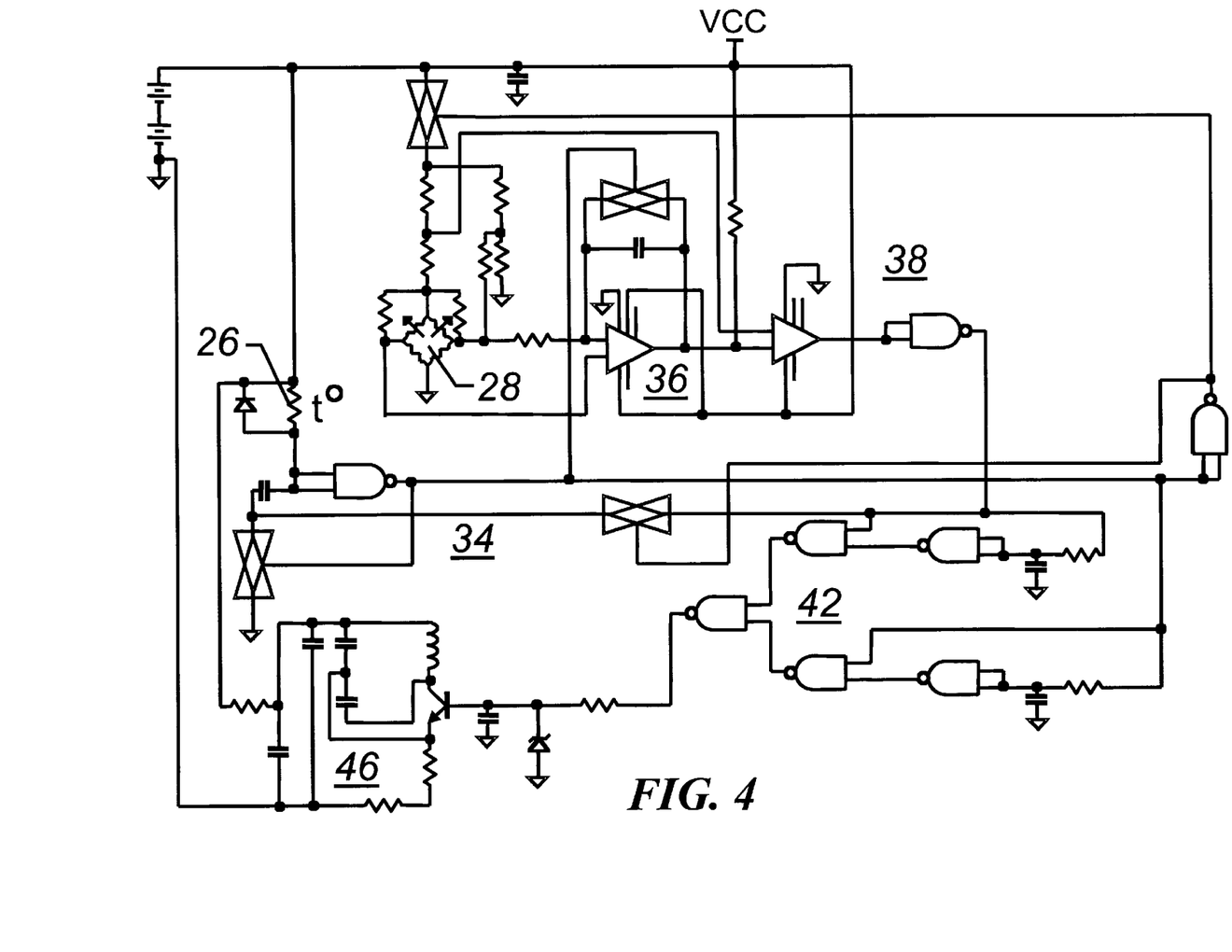
FIG. 4 is a circuit schematic of a preferred embodiment of the inventive transmitter circuit connected to first and second sensors of the present invention for measuring pressure and temperature.

FIG. 4 illustrates one embodiment of the transmitter circuit 32 of FIG. 3 where the first sensor 28 is a pressure transducer for measuring changes in pressure and a second sensor 26 is a thermistor for measuring temperature. The circuit operates as described above for FIG. 3.

Figure 5:
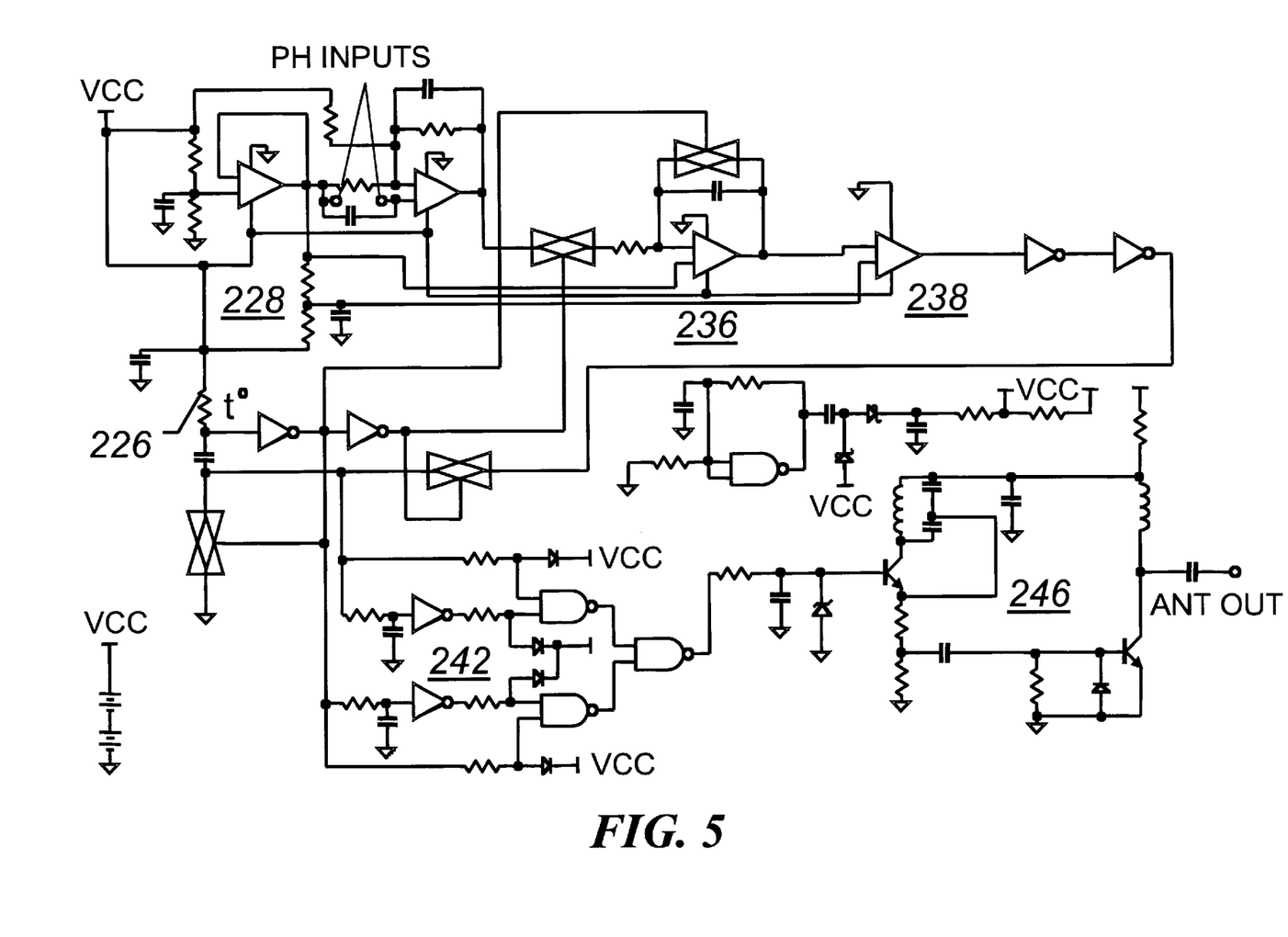
FIG. 5 is a circuit schematic of another embodiment of the inventive transmitter circuit connected to first and second sensors for measuring pH and temperature.

Another embodiment is illustrated in FIG. 5 which measures pH and temperature. The circuit of FIG. 5 operates only slightly different from the circuit of FIG. 4. The battery voltage divided by two is used as the voltage reference. An amplified pH input 228 drives the gated integrator 236 to the fixed threshold voltage. The comparator 238 detects when the threshold voltage is exceeded and converts the pH input into a pulse of varying width. The edge detector 242 converts each edge of the pulse into a short pulse. These short pulses enable an RF oscillator 246 to transmit the physiological data to the remote location. As above, this process is repeated every 100 to 500 ms depending on the value sensed by the thermistor 226. Again similar to before, the pH input is encoded by the time between the two short pulses and the temperature encoded by the repetition rate of the pulse pairs.

Figure 8:
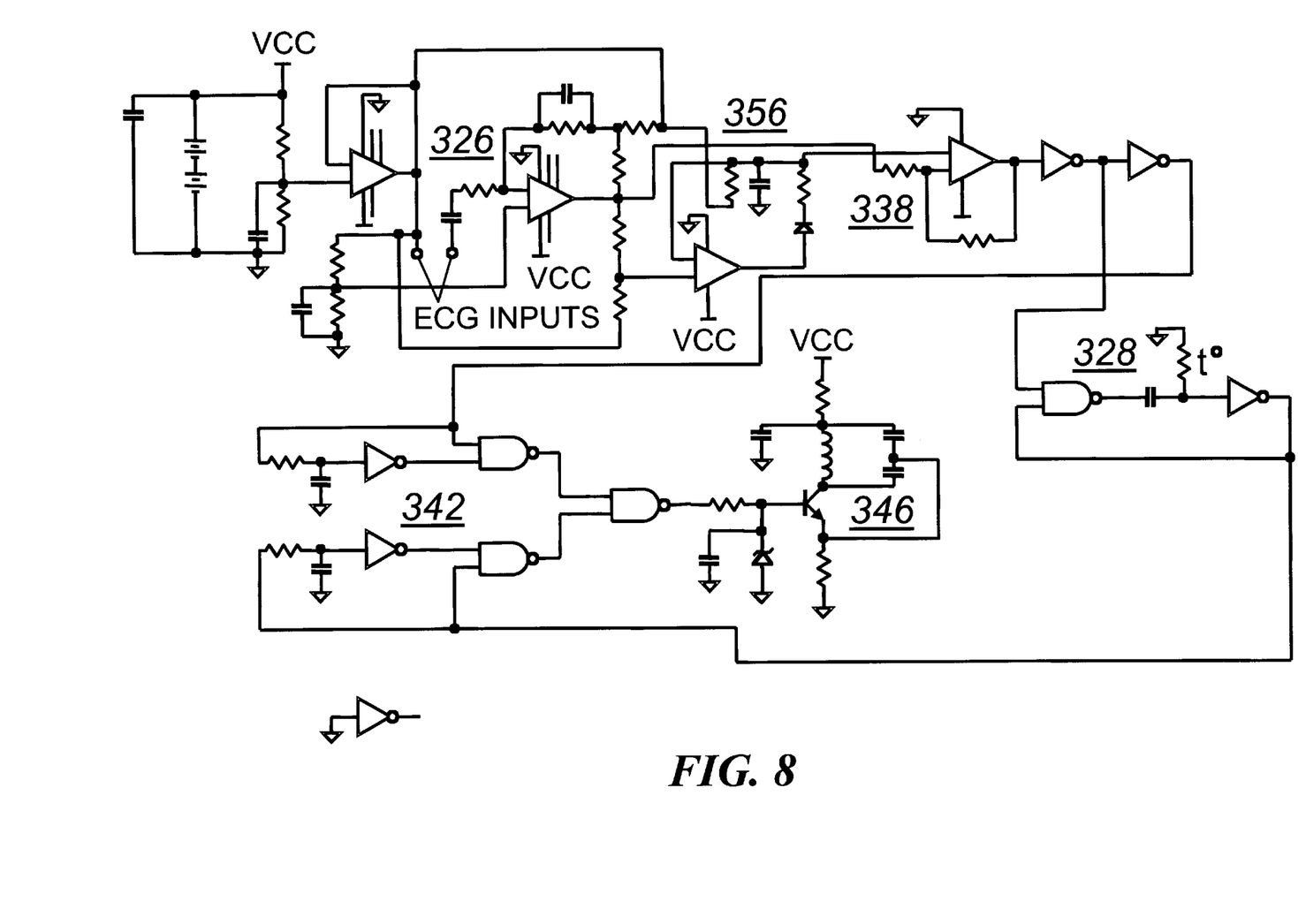
FIG. 8 is a circuit schematic of another embodiment of the inventive transmitter circuit connected to first and second sensors for measuring temperature and heart rate.

An additional embodiment is illustrated in FIG. 8 where temperature and heart rate are the measured physiological characteristics. The circuit of FIG. 8 operates in a substantially different manner than the circuits of FIGS. 4 and 5. The amplified heart rate input 326 itself drives the circuit of FIG. 8. The comparator circuit 338 compares the present signal with 60 percent of the last heart rate R-value obtained via an analog memory circuit 356. Sixty percent of the last heart rate R-value is used as a reference voltage for the comparator circuit 338 to accommodate amplitude fluctuations in the amplified heart rate input 326. The temperature sensing circuit 328 and output from the comparator circuit 338 (which is based on the amplified heart rate input) create a pulse of varying width corresponding to the temperature input. Hence, as opposed to the circuits of FIGS. 4 and 5, the edge detector 342 converts each edge of the temperature pulse into a short pulse. These short pulses enable an RF oscillator 346 to transmit the physiological data to the remote location. Note that the pulse measurements are reversed because the heart rate greatly fluctuates as opposed to the temperature. Thus, temperature is encoded by the time between the two short pulses and the heart rate is encoded by the repetition rate of the short pulse pairs.

The power consumption of FIG. 4 is approximately 30 $\mu$W. The power consumption of FIGS. 5 and 8 is respectively approximately 18 and 30 $\mu$W. One of ordinary skill would understand the logic configurations of the embodiments shown in FIGS. 4, 5 and 8.

Returning to FIG. 1, the transmitter 12 preferably uses Pulse Interval Modulation (PIM) to transmit 48 physiological characteristic data, such as temperature and pressure information in the preferred embodiment, out of the biological environment 20 of the uterus to an antenna 50 of a remotely located receiver 14. The transmission 48 uses a RF carrier frequency in a suitable biomedical range such as 174 MHz to about 214 MHz. PIM includes a pair of short pulses (RF bursts) transmitted at a frequency of about 1 Hz to about 4 Hz. The interval between the two pulses of a pair is proportional to a first physiological characteristic. The interval between successive pulse pairs is proportional to a second physiological characteristic measured or sensed. For the example of monitoring and evaluating postoperative preterm labor and fetal health, the preferred first and second physiological characteristics are pressure and temperature, respectively. A low data rate and non-continuous nature of the PIM encoding scheme conserves power and guarantees a lifetime of several months for the transmitter 12. The data rate is sufficient for monitoring intra-uterine contractions, which occur over several minutes. The range of transmission 48 of the RF carrier frequency depends on the position of the transmitter 12 in the body, the biological environment, and the orientation of a receiving antenna 50, typically in the range of about 3 to about 10 feet.

Figure 6:
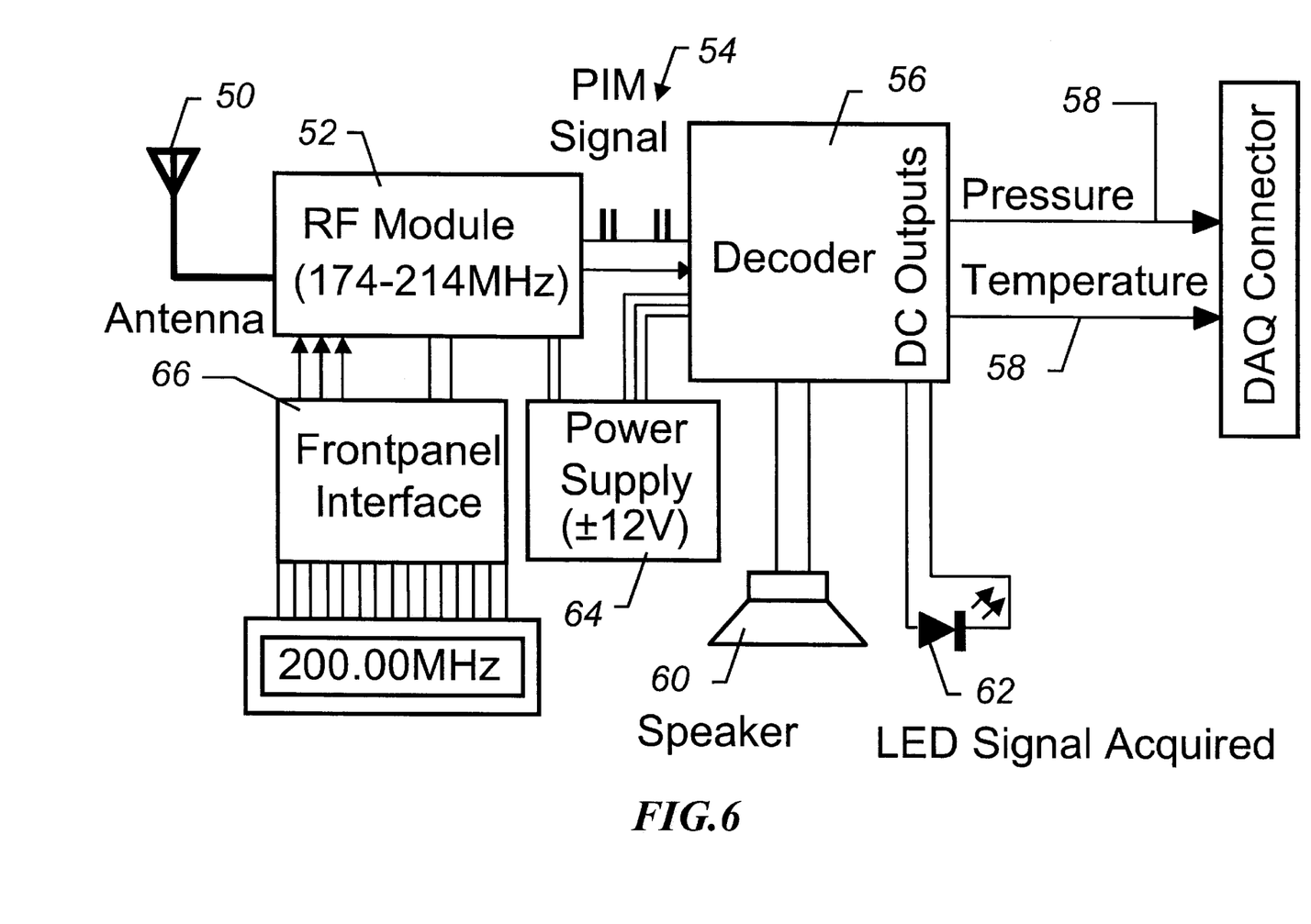
FIG. 6 is a block diagram of the receiver circuit of the present invention.

The receiver 14 converts the pulse interval modulated RF signal into a digital pulse stream, which in the preferred embodiment is then decoded into voltages proportional to temperature and pressure as generally illustrated in FIG. 6. As currently configured, each receiver channel can process the physiological characteristic data signals of one pill transmitter. The antenna 50 receives the transmission 48 of the PIM signal. An RF module 52 demodulates low-frequency PIM signals. For example and not limitation, a commercially available receiver from Konigsberg Instruments model TR8 used as the RF module 52 has been modified to demodulate low-frequency PIM signals. The digital output signal 54 of the RF module 52 is then processed by a decoder 56, which uses integrators and sample-and-hold circuits to convert the varying time intervals into DC voltage outputs 58. A speaker 60 and LED 62 are connected to the decoder 56 for auditory and visual feedback of tuning the receiver. A power supply 64 is connected to the decoder 56, RF module 52, and a computer 66.

The telemetry system 10 includes a data acquisition card 16, such as a conventional PCMCIA card, from National Instruments of Austin, Tex. to digitize the analog pressure and temperature data from the biotelemetry receiver 14 into the computer 66. A commercially available graphical programming language for virtual instrumentation called LabVIEW (trademark of National Instruments of Austin, Tex.) displays, analyzes, and stores the data as a function of time on the computer 66. For the fetal application of the preferred embodiment, the LabVIEW software can be configured to perform peak detection (contractions), integrate the area under the pressure-time curve, and determine the frequency of contractions. Furthermore, it enables the doctor to view the frequency spectrum of the pressure-time curve and a histogram of the intervals between contractions. This information will help surgeons determine and quantify the onset of preterm labor more accurately, which is essential for effective treatment.

Figure 7A:
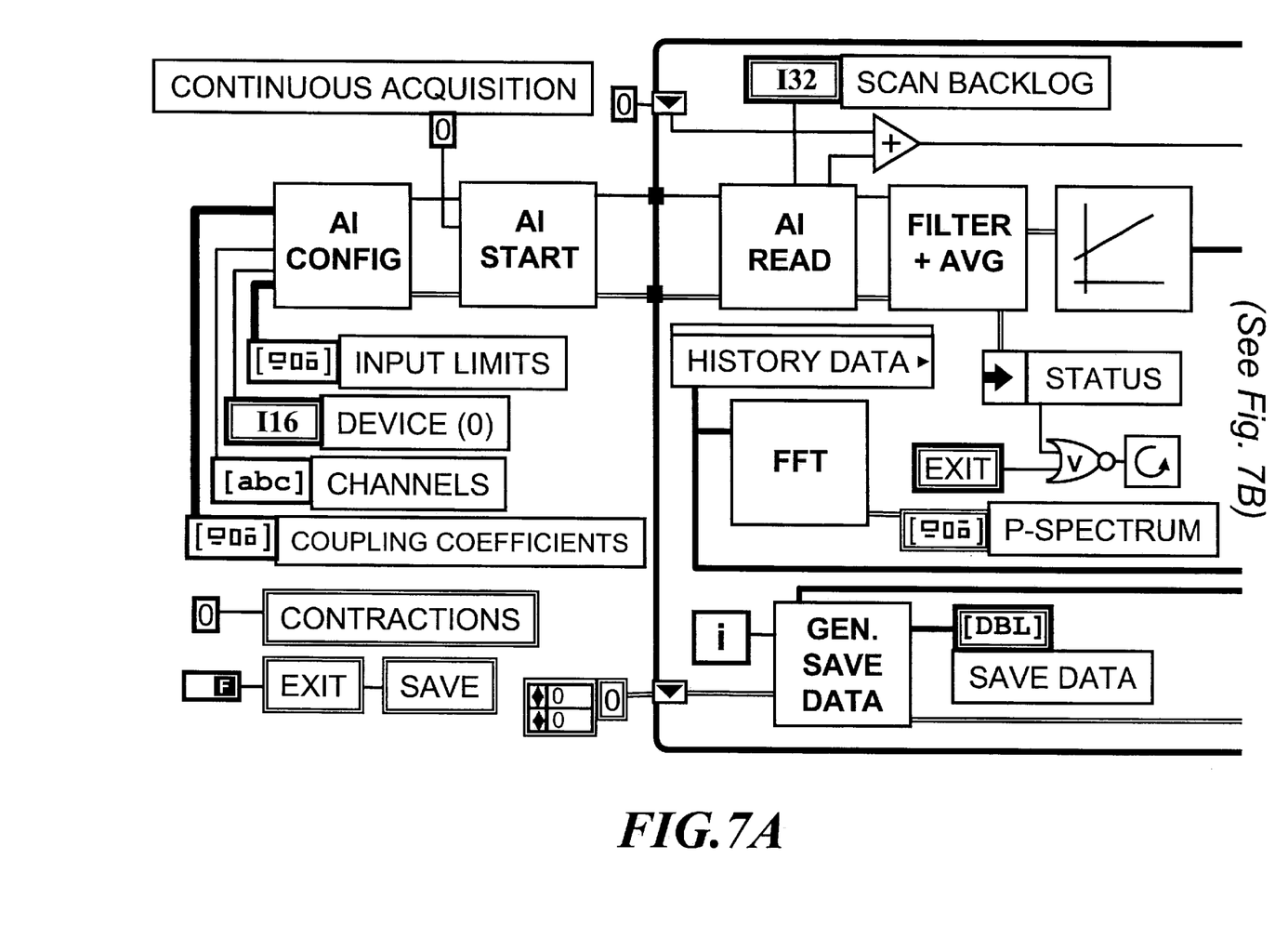
FIG. 7 is a block diagram of the virtual control and indicators of a software program implementing the present invention.
Figure 7B:
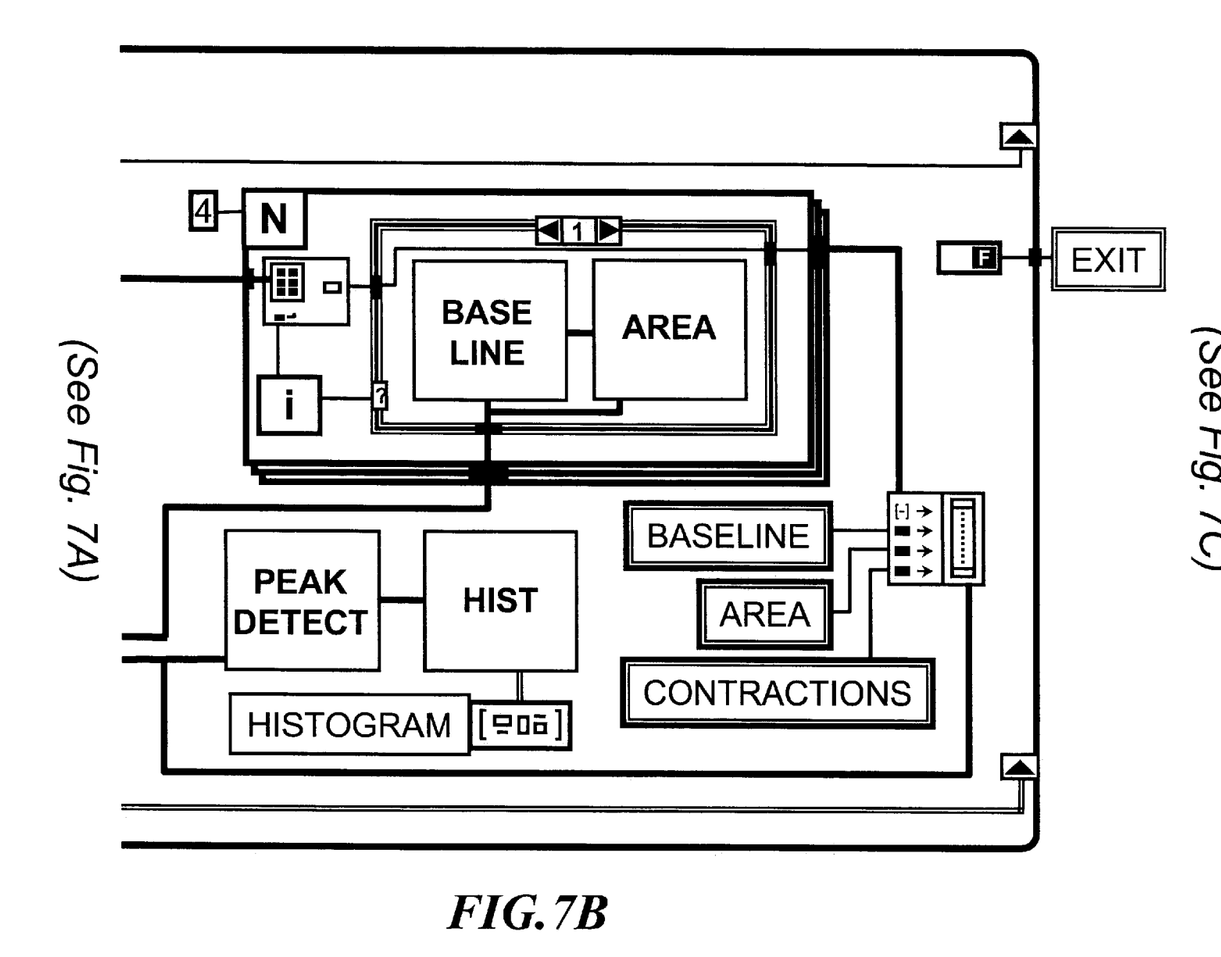
Figure 7C:
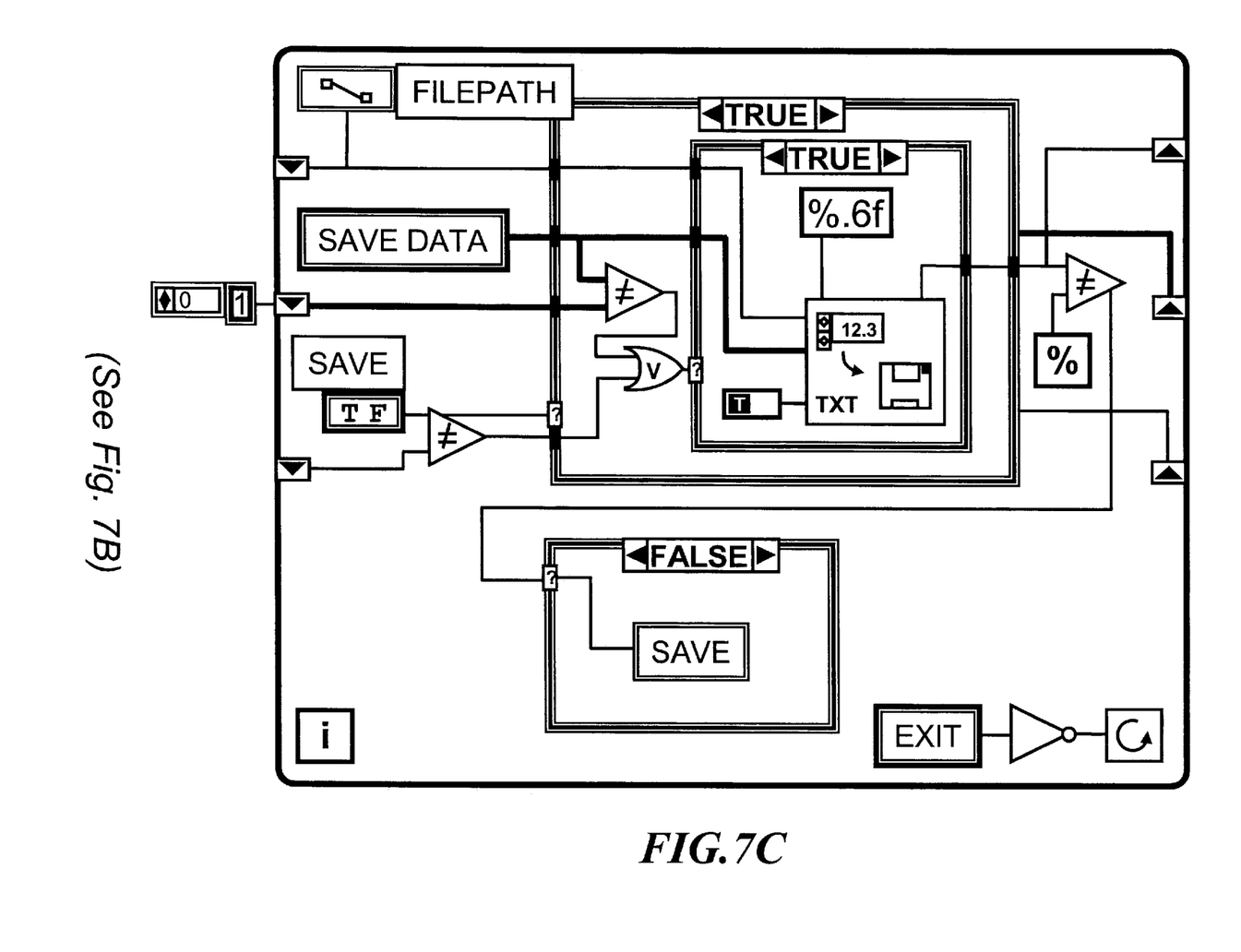

LabVIEW provides a virtual front panel and graphical user interface containing virtual controls and indicators (buttons, switches, lights, gauges, graphs, etc.) that appear as symbols in the block diagram of FIG. 7. These symbols are graphically connected ('wired') to function symbols inside the block diagram. The front panel can show any combination of graphs displaying physiological data vs. time and data analysis routines. Digital displays and out-of-range indicators are located next to each graph. The front panel also provides controls for defining sample rate, update rate, and save rate.

FIG. 7 illustrates a main loop (while-loop) which is initialized at program start with variables outside the loop (see block diagram). Once the program is running, this loop continuously samples, displays, and analyzes the physiological input data. The input data is acquired from the data acquisition card 16 using the high-level LabVIEW function "AI-Read". The sampling and update-rates can be user-defined on the front-panel before the program is run. The raw data is filtered, averaged and scaled. Four out of eight channels are graphically displayed on the front panel. For each channel, the program determines if the value is outside a preset range and color-coded indicators display the result every time the graphs are updated.

The program performs several real-time analysis routines on the last 60 minutes of recorded data or any other predetermined time period for one of the displayed channels. For instance, the analysis includes pressure changes during fetal monitoring. First, the program determines a baseline from the first data samples. The baseline is used as a relative reference level for peak detection. The peak detection algorithm is flexible and adjusts to a wide range of waveforms, peak durations, and noise levels. During fetal monitoring, each peak corresponds to a contraction. The program counts all peaks that occurred over the last 60 minutes. It also measures the times between successive peaks and displays the results in a histogram. This feature determines periodicity. Another routine performs an online fast Fourier transform on the data and displays the resulting spectrum. Finally, the area between the signal and its baseline is integrated and displayed. This value serves as a general indicator for 'activity'. During fetal monitoring, the area underneath the pressure curve can be used to characterize labor.

All routines described above are performed once during each "update" of the graphical displays, typically every second. The update rate does not limit the sampling rate. Data can be sampled faster than the graphical displays are updated. Sampling, filtering, scaling, and data analysis are controlled by the main 'while-loop' in FIG. 7. A second 'while-loop', is responsible for the storage of data. The second loop gets its data from the main loop and generates a temporary spreadsheet array. It saves the data after a predefined number of data samples have been collected in a temporary array.

The described program has a variety of unique features which focus on analyzing signals of 'unknown' nature. A wide range of diagnostic 'tools'can be applied to the signal and used to characterize it. It allows the analysis of signal range, baseline, peaks, area, spectrum, and periodicity in real-time. Furthermore, the program uses unique digital signal processing algorithms for baseline/peak detection and peak-to-peak interval calculation. For ease of observation, the range indicators are color-coded.

The biotelemetry system 10 of the present invention is capable of processing the signals of two transmitters operating at two different frequencies. Information on pressure, temperature, and pH, for instance, could be obtained by either implanting one transmitter that can measure pressure, temperature, and pH, or by implanting two transmitters, a pressure/temperature transmitter and a pH/temperature transmitter.

The applications of the transmitters and biotelemetry system of the present invention are numerous and go beyond fetal surgery. As the transmitters can be designed slightly smaller so that a pill transmitter can be swallowed, they could easily provide information on stomach-acid, for instance, without the need for surgery. Intestinal pressure changes could be monitored as well. Other physiological characteristics such as, but not limited to, heart rate, blood oxygen, carbon dioxide, ECG, EMG, pH, and glucose, as well as various ions like potassium, calcium, and sodium can be measured by the present invention. The, biotelemetry devices and system herein can be used to measure and transmit physiological parameters from biological subjects during spaceflights as well.

Therefore, the present invention discloses a biotelemetric system that utilizes a small, modular, low-power/long-life, pill-shaped implantable biotelemeter capable of continuously sensing physiological characteristics over a period of up to nine months or slightly more. Further, the present invention discloses the integration of ion-selective microelectrode sensors into a biotelemetric system.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A telemetry system for measuring at least two physiological characteristics from a position implanted inside a living subject and transmitting the individual characteristics as physiological data to a remote location, the system comprising:

a transmitter for sensing and transmitting physiological data in a pulse interval modulated signal;

a receiver configured to receive and convert the pulse interval modulated signal into digital pulse stream, the receiver decoding the digital pulse stream into voltages proportional to the individual characteristics of the physiological data;

a data acquisition card configured to digitize the physiological data; and a signal processing system for display and storage of the individual characteristics of the physiological data over time.

2. The telemetry system of claim 1 wherein the signal processing system includes a computer configured to perform multiple real-time analysis routines on a predetermined time period for one or more of the individualized characteristics of the physiological data.

3. The telemetry system of claim 2 wherein the signal processing system includes a computer configured to update the individualized characteristics of the physiological data at a predetermined rate and periodically generate a temporary spreadsheet array.

4. The telemetry system of claim 3 wherein the signal processing system includes a computer configured to save the physiological data after a predefined number of data samples have been collected in the temporary spreadsheet array.

5. The telemetry system of claim 2 wherein the subject is a fetus and the configuration of the computer signal processing system determines a baseline from the first physiological data samples, references the baseline at a defined level for detection of peaks, and correlates each peak to a contraction.

6. The telemetry system of claim 5 wherein the computer is further configured to accumulate all peaks over a predetermined time period and measure the times between successive peaks to determine periodicity.

7. The telemetry system of claim 6 wherein the computer charts said determined contraction periodicity.

8. The telemetry system of claim 5 wherein the computer is further configured to perform a fast Fourier transform on the physiological data and display the resulting spectrum.

9. The telemetry system of claim 5 wherein the computer is further configured to integrate and display the area between the signal and its baseline to characterize labor.

10. The telemetry system of claim 1 wherein the receiver comprises an integrator and sample-and-hold circuit to convert varying time intervals of the physiological data into DC voltage outputs.

11. The telemetry system of claim 1, wherein the transmitter includes a first sensor for a first physiological characteristic and a second sensor for a second physiological characteristic, and wherein said pulse interval modulated signal includes pairs of short pulses wherein the interval between the two pulses of a pair is proportional to a first physiological characteristic and the interval between successive pulse pairs is proportional to a second physiological characteristic.

12. A method of measuring at least two physiological characteristics from a device implanted in a position inside a living subject and transmitting the individual characteristics a physiological data to a remote application, the method comprising:

sensing and transmitting physiological data in a pulse Interval modulated signal to the remote location;

receiving and converting the pulse interval modulated signal into a digital pulse stream into voltages proportional to the individual characteristics of the physiological data;

digitizing the physiological data; and displaying and storing of the individual characteristics of the physiological data over time.

13. The method of claim 12 wherein receiving and converting step includes converting the pulse internal modulated signal into a digital pulse stream and decoding the digital pulse stream into voltages proportional to the individual characteristics of the physiological data.

14. The method of claim 12 wherein the displaying and storing step includes performing multiple real-time analysis routines on a predetermined time period for one or more of the individualized characteristics of the physiological data.

* * * * *